United States Patent [19]
Schad

[11] 3,986,501
[45] Oct. 19, 1976

[54] APPARATUS FOR ALLEVIATING FOOT-DROP

[76] Inventor: Jerome G. Schad, R.D. No. 3, Evans City, Pa. 16033

[22] Filed: Sept. 15, 1975

[21] Appl. No.: 613,213

[52] U.S. Cl. ................................. 128/80 E
[51] Int. Cl.² .................................. A61F 3/00
[58] Field of Search .............. 128/80 E, 80 R, 84, 128/87

[56] References Cited
UNITED STATES PATENTS

| | | | |
|---|---|---|---|
| 1,402,282 | 1/1922 | Chevrier | 128/80 E |
| 3,527,209 | 9/1970 | Baker | 128/80 E |

FOREIGN PATENTS OR APPLICATIONS

| | | | |
|---|---|---|---|
| 493,196 | 10/1919 | France | 128/80 E |
| 523,538 | 10/1921 | France | 28/80 E |

*Primary Examiner*—John D. Yasko

[57] ABSTRACT

Apparatus for alleviating foot-drop having a rigid vertical member which is curved and arched to conform to the rear of the calf of the human leg. The bottom of the vertical member has a cup-like shape to conform to the heel of the foot without extending under the heel. A V-strap member is connected at the top of the vertical member for the purpose of insertion at the shoe near the dorsum portion of the foot for lifting the dorsum of the foot when the heel is raised.

6 Claims, 4 Drawing Figures

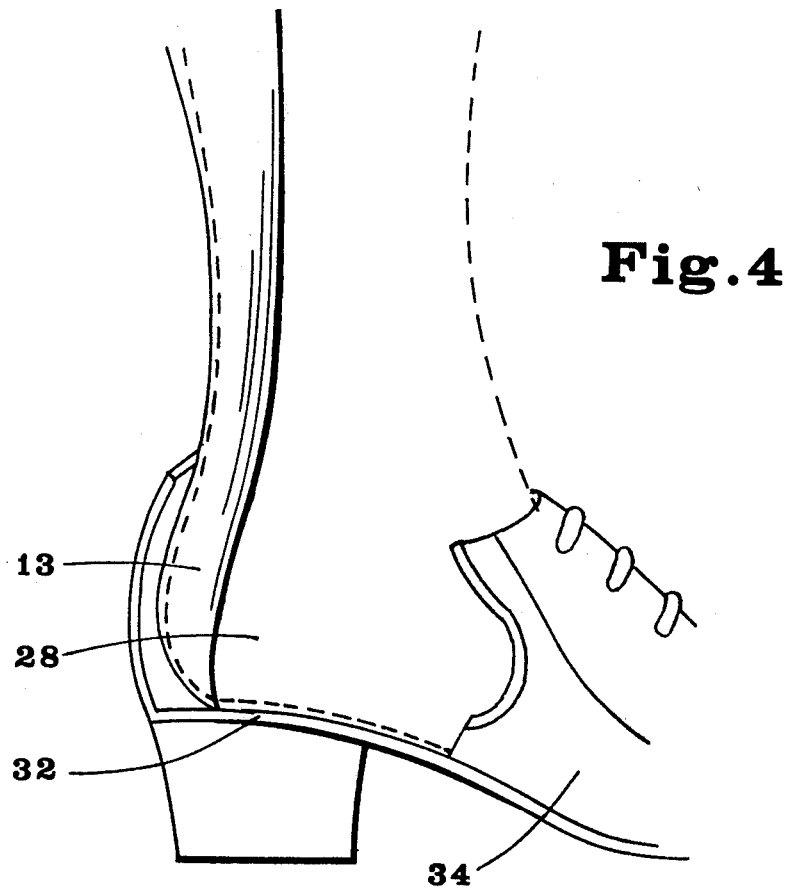

APPARATUS FOR ALLEVIATING FOOT-DROP

PROBLEM PRESENTED TO THE INVENTOR

This invention relates to an apparatus for the alleviation of mild foot-drop. Mild foot-drop refers to a condition of foot-drop which is uncomplicated by the presence of spasticity or severe lateral instability. It is confined to a disability of the anterio-posterior plane where the foot tends to hang in a planter-flexed position which prevents or interfers with normal ambulation. An individual with mild foot-drop will require the use of other muscles thoroughout the body to lift the dorsum portion of the foot. It requires muscles of the leg and the remainder of the torso. A person having mild foot-drop is noticeable by the manner in which the foot is raised which appears to require great effort and requires the exertion of a directly upward force resulting in a limp. Because of the additional muscular effort which is needed to raise the foot during normal walking the individual becomes fatigued more than otherwise would be the situation in a person without foot-drop.

THE PRIOR ART

There have been a number of mechanical devices for alleviating foot-drop. These have included short-leg braces having metal uprights, a calf cuff, a metal stirrup attached to the shoe and ankle joints and other features such as a spring lift. Other devices have employed spring wire as uprights and relied upon the spring action of the uprights to produce a foot lifting action. Other devices have included a stirrup attached to a metal foot plate with the lower end inserted within the shoe. These devices have all suffered disadvantages because of their weight which taxes the strength of the leg. They are also bulky and tend to cause injury to the opposite ankle. The leg is often confined excessively thereby placing a limitation on the foot and ankle movement which tends to further reduce the remaining functional capacity of the patient and thereby expanding the existing disability which the apparatus is intended to alleviate.

My design provides a structure which overcomes these disadvantages. It gives the patient the ability to insert and use the device without professional aid. This is primarily due to its simplistic design.

DESCRIPTION OF THE PREFERRED EMBODIMENT

I provide an apparatus for alleviation of human foot-drop for use with a heel, rear of a calf and a shoe comprising a rigid vertical member having a longitudinal axis, a top portion and a bottom portion, the member is curved concavely throughout its longitudinal axis to conform to a shape of the rear of the calf, the member is arched along the longitudinal axis from the bottom to the top to conform to an arc of the rear of the calf in the leg from a bottom of a heel platform of the shoe to a point along the rear of the calf, the bottom portion of the member is cupped to conform to the heel without extending under the heel, the bottom portion is intended to be inserted against the heel and into the shoe between the heel and the shoe; and a V-strap member having two ends each fastened at opposite sides near the top of the vertical member, the strap is intended to be connected to the shoe at a dorsum portion of a foot forming a V shape with a vertex near the dorsum of the foot.

Other details, objects and advantages of this invention will become apparent as the following description of the present preferred embodiment proceeds.

In the accompanying drawings, I have shown a present preferred embodiment of the invention in which:

FIG. 4 is a sectional view of the bottom portion of the apparatus in combination with the heel and the shoe.

Figure 1:
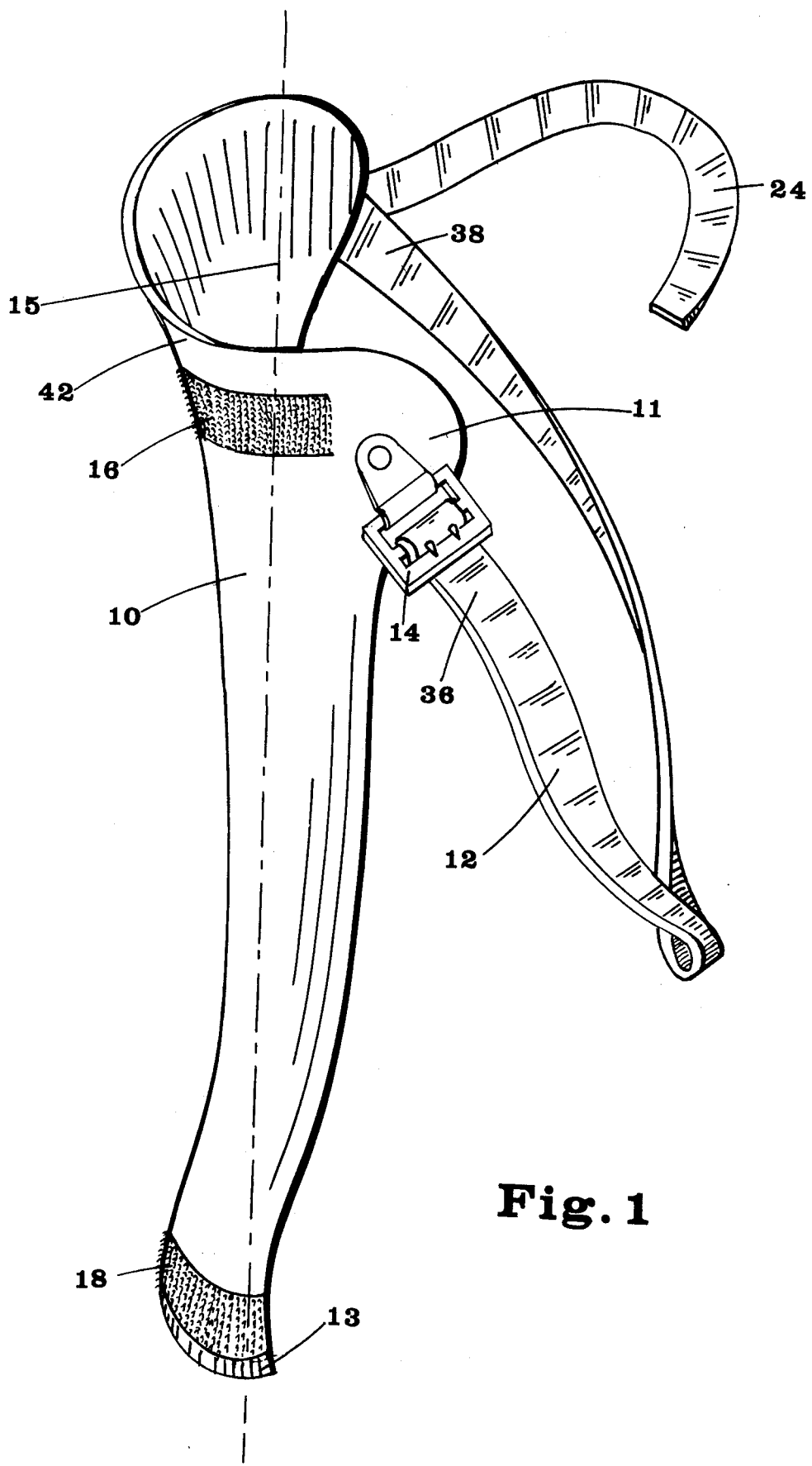
FIG. 1 is a perspective view of the apparatus.
Figure 2:
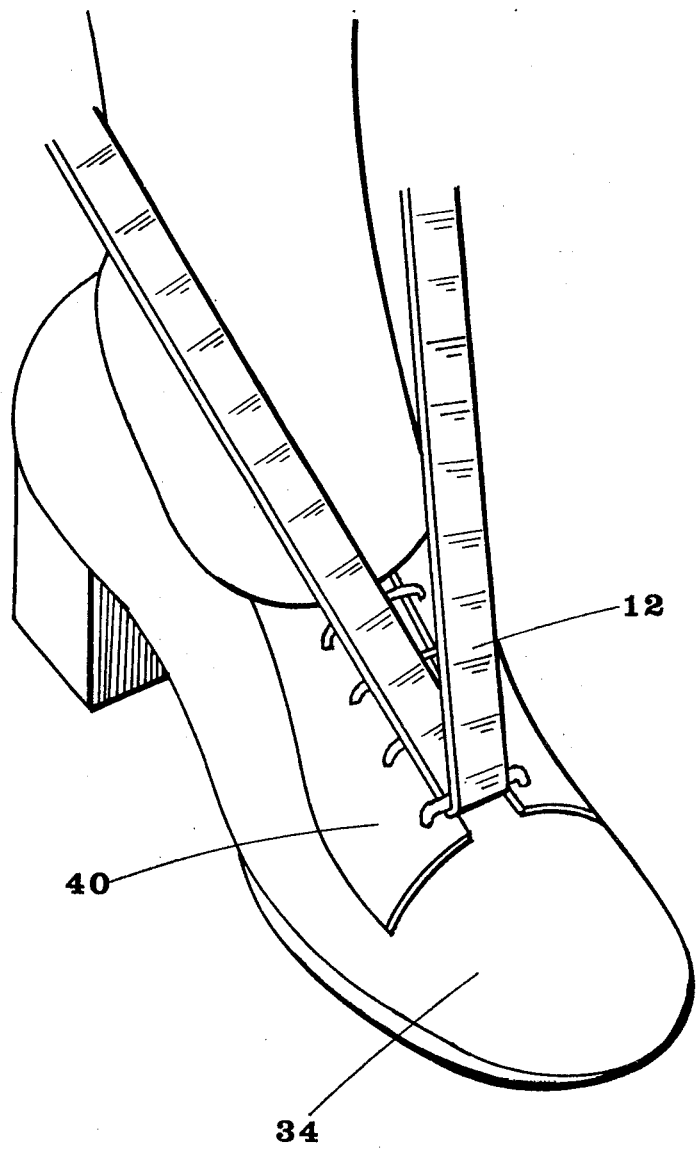
FIG. 2 is a perspective view showing the V-strap in combination with the shoe from the front.

Referring to the figures, a rigid vertical member 10 has a top portion 11 and a bottom portion 13. The member 10 is curved concavely about its longitudinal axis 15. The purpose of the concave configuration is to conform to the shape of the rear of the calf 30. The vertical member 10 is arched along the longitudinal axis 15 from the bottom portion 13 to the top portion 11 to conform to the natural arc of the rear of the calf 30 in the leg. The arc begins from a point at the bottom of the heel platform 32 of the shoe 34. The bottom portion 13 is cupped to conform to the heel 28 of the foot without extending under the heel 28 as shown in FIG. 4. The bottom portion 13 is intended to be inserted against the heel of the shoe 34 between the heel 28 and the shoe 34. A V-strap member 12 which is of a suitable elastomer material has two ends 36 and 38. These ends 36 and 38 are fastened by a suitable means which can include a buckle 14 or a hook and loop type fastener at opposite sides of the vertical member 10 near the top portion 11. The strap 12 is intended to be looped to the shoe 34 near the dorsum portion 40 of the foot. This forms a V shape with a vertex near the dorsum 40.

To provide additional support a circumferential strap 24 with one end connected at the top portion 11 at one side of the vertical member 10 is used for partially encircling the front of the calf 30 and is attached to the opposite side of the vertical member 10 by a suitable means such as a hook and loop fastener 16. The bottom portion 13 is narrower than the top portion 11 of the vertical member 10. The top portion 11 has a curved portion 42 which is arched away from that portion intended to engage the rear portion of the calf 30. In order to prevent the vertical member 10 from slipping between the shoe 34 at the heel 28 an abrasive means such as the type normally known as hook and loop fastener 18 is positioned near the bottom portion 13.

Figure 3:
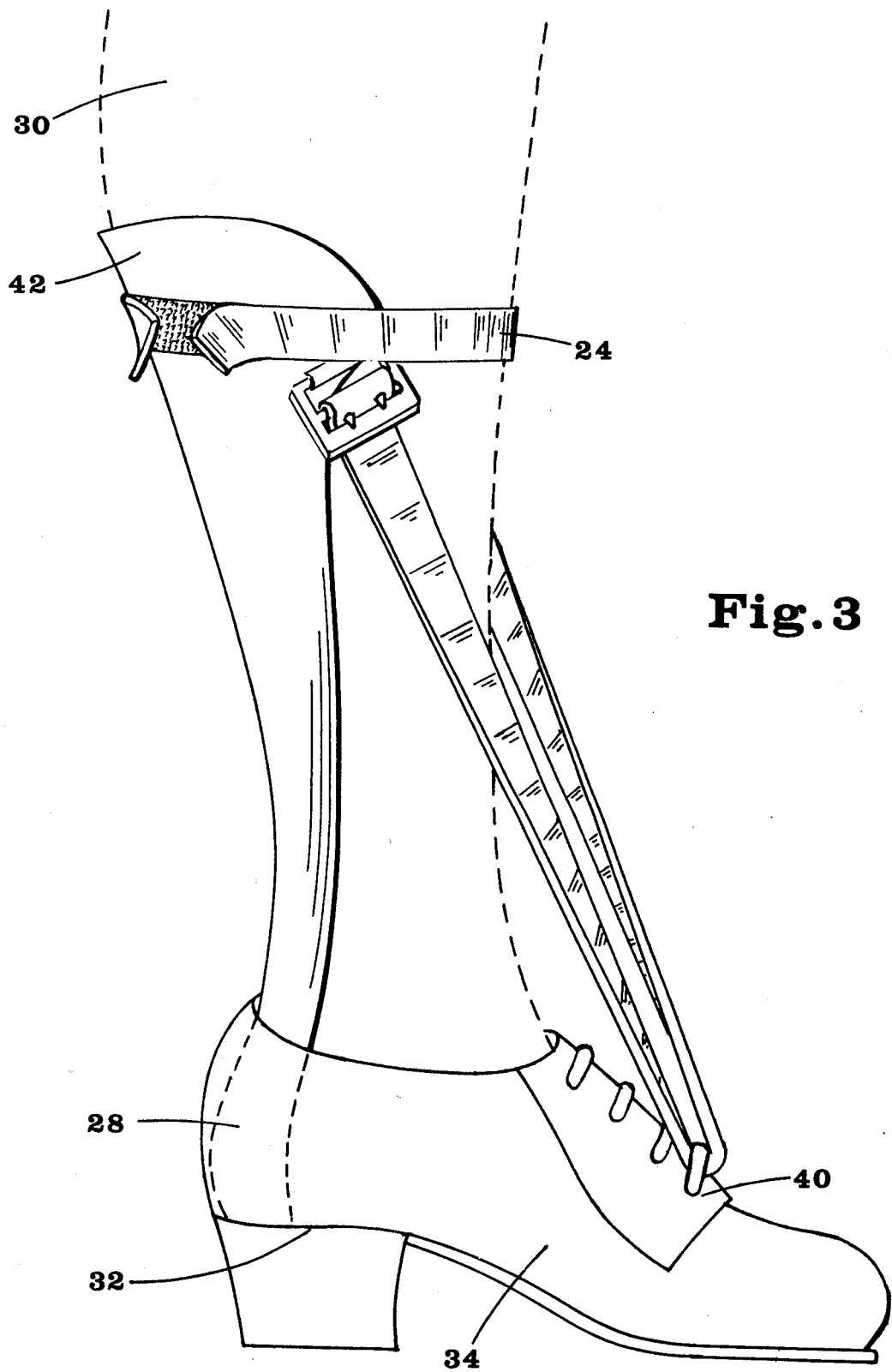
FIG. 3 is a perspective view of the apparatus showing its use with the shoe, the calf and the heel.

As can be seen in FIG. 3 the vertical member 10 with the V-strap 12 looped at the dorsum 40 of the foot assists in lifting the dorsum 40 whenever the heel 28 is raised thereby alleviating limp which is caused by mild foot-drop.

I claim:

1. Apparatus for alleviation of human foot-drop for use with a heel, rear of a calf and a shoe comprising:
    a. a rigid vertical member having a longitudinal axis, a top portion and a bottom portion, the member is curved concavely throughout its longitudinal axis to conform to a shape of the rear of the calf, the member is arched along the longitudinal axis from the bottom to the top to conform to an arc of the rear of the calf in the leg from a bottom of a heel platform of the shoe to a point along the rear of the calf, the bottom portion of the member is cupped to conform to the heel without extending under the heel, the bottom portion is intended to be inserted against the heel and into the shoe between the heel and the shoe; and b. a V-strap member having two ends each fastened at opposite sides near the top of the vertical member, the strap is intended to be connected to the shoe at a dorsum portion of a foot forming a V shape with a vertex near the dorsum of the foot.

2. The apparatus as recited in claim 1 wherein the V-strap member is an elastomer material.

3. The apparatus as recited in claim 1 including a circumferential strap having one end connected at the top portion at one side of the vertical member for the purpose of partially encircling a front of the calf and attaching the other end of the circumferential strap to the opposite side of the vertical member at its top portion.

4. The apparatus as recited in claim 1 wherein the bottom portion is narrower than the top portion.

5. The apparatus as recited in claim 1 wherein the top portion has a curved portion which is arched away from that portion which is intended to engage the rear portion of the calf.

6. The apparatus as recited in claim 1 including a means positioned near the bottom portion of the vertical member and on the opposite side of the portion which engages the heel for preventing the vertical member from slipping between the heel and the shoe.

* * * * *